US 9,204,915 B2

(12) United States Patent
Arthur et al.

(10) Patent No.: US 9,204,915 B2
(45) Date of Patent: Dec. 8, 2015

(54) DEVICE FOR PERFORMING A SURGICAL PROCEDURE AND METHOD

(71) Applicant: KYPHON SARL, Neuchatel (CH)

(72) Inventors: Amy L. Arthur, Mountain View, CA (US); Hester Chan, Sunnyvale, CA (US)

(73) Assignee: KYPHON SARL, Neuchatel (CH)

( * ) Notice: Subject to any disclaimer, the term of this patent is extended or adjusted under 35 U.S.C. 154(b) by 364 days.

(21) Appl. No.: 13/830,537

(22) Filed: Mar. 14, 2013

(65) Prior Publication Data

US 2014/0276868 A1  Sep. 18, 2014

(51) Int. Cl.
*A61B 17/88* (2006.01)
*A61B 17/00* (2006.01)

(52) U.S. Cl.
CPC .......... *A61B 17/8855* (2013.01); *A61B 17/8811* (2013.01); *A61B 17/8819* (2013.01); *A61B 2017/0023* (2013.01); *A61B 2017/00557* (2013.01)

(58) Field of Classification Search
CPC ........... A61B 17/8855; A61B 17/8811; A61B 17/8819
See application file for complete search history.

(56) References Cited

U.S. PATENT DOCUMENTS

| | | | |
|---|---|---|---|
| 3,746,003 A | 7/1973 | Blake et al. | |
| 5,320,605 A | 6/1994 | Sahota | |
| 5,759,172 A | 6/1998 | Weber et al. | |
| 5,797,869 A | 8/1998 | Martin et al. | |
| 5,961,536 A | 10/1999 | Mickley et al. | |
| 2012/0289968 A1 | 11/2012 | Rabiner et al. | |
| 2013/0165942 A1* | 6/2013 | Tan-Malecki et al. | 606/94 |

* cited by examiner

*Primary Examiner* — David Bates
(74) *Attorney, Agent, or Firm* — Sorell Lenna & Schmidt LLP

(57) ABSTRACT

A device includes an inflatable member extending between a first end and a second end. An inner surface of the inflatable member defines a first passageway in the first end and a chamber in the second end. An inner member is disposed in the first passageway and extends through the chamber. The inner member includes an inner surface defining a second passageway. A second end of the inflatable member is bonded to an outer surface of the inner member. A guide is member disposed in the second passageway. An outer member includes a first end having a projection including a threaded outer surface. The outer member includes an inner surface defining a third passageway having the inflatable member disposed therein. A cap includes a threaded inner surface that engages the threaded outer surface of the projection. Methods of use are provided.

21 Claims, 4 Drawing Sheets

DEVICE FOR PERFORMING A SURGICAL PROCEDURE AND METHOD

TECHNICAL FIELD

The present disclosure generally relates to medical devices for the treatment of musculoskeletal structures, and more particularly to a surgical system and method employing a cannulated inflatable bone tamp for fracture reduction.

BACKGROUND

Height loss is commonly associated with fractures, such as, for example, spinal fractures, typically referred to as vertebral compression fractures. A large segment of osteoporotic patients experience vertebral compression fractures, with an estimated 700,000 such fractures occurring annually. Kyphoplasty is a minimally invasive procedure that is used to treat vertebral compression fractures using a combination of vertebroplasty utilizing a bone void filler, such as, for example, bone cement with balloon catheter technology. The kyphoplasty procedure restores height of the collapsed spinal bone which diminishes associated back pain.

Kyphoplasty procedures may also be used to treat fractures in other areas of a patient's body, such as, for example, a distal radius of the patient, such as, for example Colles' fractures. To treat a distal radius fracture using a kyphoplasty procedure, an inflatable bone tamp (IBT) is utilized. The IBT is used to percutaneously reduce comminuted, articular depressions in a controlled manner. Fracture morphologies, such as, for example, "die-punch" fractures are especially suited for correction by an IBT. IBTs are deployed to a surgical site, such as, for example, a bone defect through a working cannula. IBTs create well-defined voids. After the void is created by the IBT, the IBT is removed from the cannula and a material, such as, for example a bone void filler is delivered through the cannula and into the void. The bone void filler may be used in conjunction with percutaneous pins, ex-fixes, plates and/or screws for fracture fixation.

In conventional kyphoplasty procedures, the IBT are inserted adjacent the bone defects by inserting the IBT through a cannula. An inflatable member of the IBT is expanded to create a void in or adjacent the bone defect. After the IBT creates the void, the IBT is removed from the cannula and bone void filler is delivered through the cannula to the void in order to at least partially fill the void. This disclosure describes an improvement over these prior art technologies.

SUMMARY

Accordingly, a surgical system and method for correction of a bone injury or disorder are provided. In one embodiment, in accordance with the principles of the present disclosure, the surgical system includes a device for performing a surgical procedure. The device comprises an inflatable member extending along a longitudinal axis between a first end having a first opening and a second end having a second opening. An inner surface of the inflatable member defines a first passageway in the first end and a chamber in the second end. The first and second openings are in communication with the first passageway. An inner member is disposed in the first passageway and extends through the first and second openings. The inner member includes an inner surface defining a second passageway. A first end of the inner member includes a first opening and a second end of the inner member has a second opening. The first and second openings of the inner member are in communication with the second passageway. The second end of the inflatable member is bonded to an outer surface of the inner member. A guide member is disposed in the second passageway and extends through the first and second openings of the inner member. An outer member comprises a first end having a projection including a threaded outer surface. The outer member includes an inner surface defining a third passageway having the inflatable member disposed therein. A cap includes a threaded inner surface engaging the threaded outer surface of the projection.

In one embodiment, in accordance with the principles of the present disclosure, the surgical system includes a device comprising an inflatable member extending along a longitudinal axis between a first end and a second end having an opening. An inner surface of the inflatable member defines a first passageway in the first end and a chamber in the second end. The opening is in communication with the first passageway. An inner member is disposed in the first passageway and extends through the opening. The inner member includes an inner surface defining a second passageway. A second end of the inner member has an opening that is in communication with the second passageway. The second end of the inflatable member being bonded to an outer surface of the inner member. A guide member is disposed in the second passageway and extends through the opening of the inner member. A stopper engages the inflatable member to prevent the inflatable member from moving proximally relative to the guide member.

In one embodiment, in accordance with the principles of the present disclosure, the surgical system includes a device comprising an inflatable member extending along a longitudinal axis between a first end having a first opening and a second end having a second opening. An inner surface of the inflatable member defines a first passageway in the first end and a chamber in the second end. The first and second openings are in communication with the first passageway. An inner member is disposed in the first passageway and extends through the first and second openings. The inner member includes an inner surface defining a second passageway. A first end of the inner member includes a first opening and a second end of the inner member having a second opening. The first and second openings of the inner member are in communication with the second passageway. The second end of the inflatable member is bonded to an outer surface of the inner member. A guide member is disposed in the second passageway and extends through the first and second openings of the inner member. An outer member comprises a first end having an inner surface defining a third passageway extending through the first end of the outer member having a threaded first portion and an unthreaded second portion. A second end of the outer member includes an inner surface defining a fourth passageway that is in communication with the third passageway. The inflatable member extends through the fourth passageway. An anchor member is disposed in the third passageway. The anchor member includes a threaded outer surface engaging the threaded first portion. The anchor member further includes an inner surface defining a fifth passageway having the inflatable member disposed therein.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
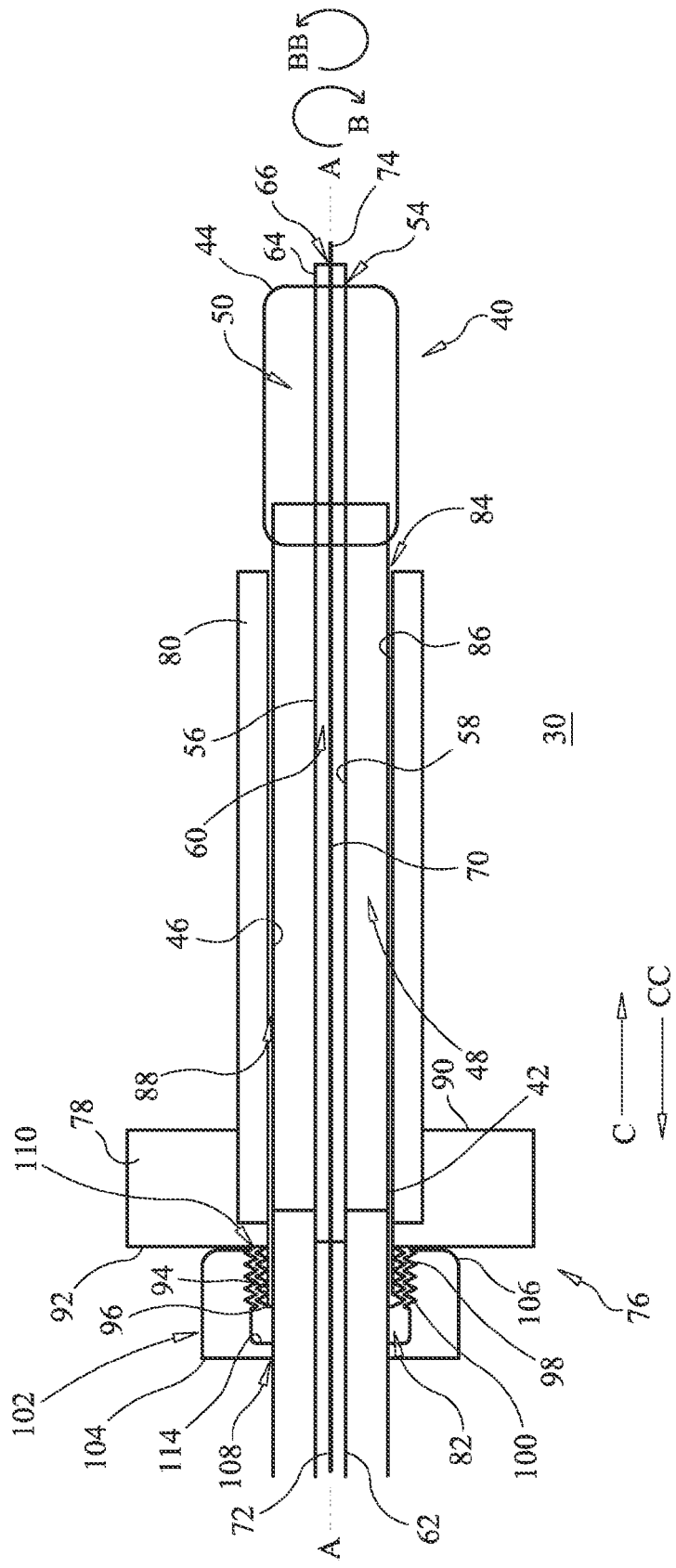
FIG. 1 is a side, cross sectional view of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a surgical system and method for bone repair. It is envisioned that the surgical system and method may be employed in applications such as for correction of fractures, depressions and breaks. For example, the surgical system and method can include an inflatable bone tamps comprising an inflatable member having various cross sectional configurations adapted to match the configuration of a bone defect, such as, for example, a fracture in a bone, such as, for example, a distal radius of a human patient. That is, the inflatable member, when in an expanded configuration, has a volume that is equal to or exceeds the volume of the bone defect such that the inflatable member can create a single void that consumes the entire bone defect. It is envisioned that this configuration is advantageous over inflatable members that create many small voids to consume one bone defect.

In one embodiment, the inflatable member has a cylindrical cross sectional configuration when the inflatable member is an expanded configuration. In one embodiment, the inflatable member has an asymmetrical cross sectional configuration when the inflatable member is an expanded configuration. In one embodiment, the inflatable member has a triangular cross sectional configuration when the inflatable member is an expanded configuration.

In one embodiment, the inflatable member having a selected cross sectional configuration is employed in a method for treating a bone defect, such as, for example a fracture, by inserting the inflatable bone member in or adjacent to the bone defect at a first selected trajectory relative to the bone and moving the expandable member to an expanded configuration such that the inflatable member creates a first void in the bone. The inflatable member is then removed from the first void and/or the bone and is inserted into the bone at a second selected trajectory relative to the bone. The inflatable member is then moved to the expanded configuration such that the inflatable member creates a second void in the bone. It is envisioned that the second void may overlap at least a portion of the first void and that the first and second voids may have a combined volume that is equal to or exceeds the volume of the bone defect such that the first and second voids consume the entire bone defect.

In one embodiment, the inflatable member has a first lobe and a second lobe that is spaced apart from the first lobe when the inflatable member is an expanded configuration. It is envisioned that the first lobe is inflatable is inflatable/deflatable independent of the second lobe, and vice versa. That is, the first lobe can have an expanded configuration while the second lobe has an unexpanded configuration and the second lobe can have an expanded configuration while the first lobe has an unexpanded configuration. In one embodiment, a multiple lumen catheter is used such that each lobe has access to its own lumen such that each lobe can be selectively inflated by delivering fluid through a respective lumen.

In one embodiment, an inflatable member having first and second lobes is employed in a method for treating a bone defect, such as, for example a fracture, by inserting the inflatable bone member in or adjacent to the bone defect and moving the expandable member to an expanded configuration such that the first lobe creates a first void and the second lobe creates a second void.

In one embodiment, the expandable member is moved relative to the bone such that the second lobe is positioned in the first void. The inflatable member is then moved to the expanded configuration such that the second lobe creates a third void adjacent the first void while the first lobe engages the first void to anchor the inflatable member relative to the bone. It is envisioned that the second lobe may be moved to the expanded configuration when the second lobe is positioned in the first void prior to moving the first lobe to the expanded configuration to create the third void such that the second lobe acts as to anchor the inflatable member relative to the bone while the third void is created.

In one embodiment, the expandable member is moved relative to the bone such that the first lobe is positioned in the second void. The inflatable member is then moved to the expanded configuration such that the second lobe creates a third void adjacent the second void while the first lobe engages the second void to anchor the inflatable member relative to the bone. It is envisioned that the first lobe may be moved to the expanded configuration when the first lobe is positioned in the second void prior to moving the second lobe to the expanded configuration to create the third void such that the first lobe acts as to anchor the inflatable member relative to the bone while the third void is created.

In one embodiment, the system includes a cannula including a first passageway including a first lumen having an inflatable member disposed therein and a second lumen having a bone filler material disposed therein. The first and second lumens each have a cylindrical cross sectional configuration and are spaced apart from one another. The inflatable member is moved through the first lumen such that at least a portion of the inflatable member is disposed adjacent a bone defect, such as, for example a fracture in a bone of a patient, such as, for example, a Colles fracture or distal radius fracture in a human patient. The inflatable member is moved to an expanded configuration such that the inflatable member creates a void in or adjacent to the bone defect. The inflatable member is then moved to an unexpanded configuration and at least a portion of the inflatable member is retracted into the first lumen. The cannula is then rotated relative to the bone defect such that the second lumen is positioned in or adjacent the void. The bone filler material is then delivered through the second lumen and into the void to at least partially fill the void.

It is contemplated that one or all of the components of the surgical system may be disposable, peel-pack, pre-packed sterile devices. One or all of the components of the surgical system may be reusable. The surgical system may be configured as a kit with multiple sized and configured components, such as, for example, inflatable members (balloons) that are preformed to have different sizes and shapes.

It is envisioned that the present disclosure may be employed to treat bones, and in particular arm bones such as a distal radius. It should be understood that the present principles are applicable to any bone structures, including but not limited to bones of the spine, legs, feet, arms, etc. It is contemplated that the present disclosure may be employed with other osteal and bone related applications, including those associated with diagnostics and therapeutics. It is further contemplated that the disclosed surgical system and methods may alternatively be employed in a surgical treatment with a patient in a prone or supine position, and/or employ various surgical approaches, including anterior, posterior, posterior mid-line, direct lateral, postero-lateral, antero-lateral, etc. approaches in the calcaneus, spine or other body regions. The present disclosure may also be alternatively employed with procedures for treating the muscles, ligaments, tendons or any other body part. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following disclosure includes a description of a surgical system for treating bone defects, such as, for example, fractures, including a cannulated inflatable bone tamp for fracture reduction. The disclosure also includes a description of related methods of employing the cannulated inflatable bone tamp. Alternate embodiments are also disclosed. Reference will now be made in detail to the exemplary embodiments of the present disclosure, which are illustrated in the accompanying figures. Turning now to FIGS. 1-4 there are illustrated components of a surgical system, such as, for example, a surgical system 30 and embodiments in accordance with the principles of the present disclosure.

The components of system 30 can be fabricated from biologically acceptable materials suitable for medical applications, including metals, synthetic polymers, ceramics and bone material and/or their composites, depending on the particular application and/or preference of a medical practitioner. For example, the components of system 30, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of balloon system 20 may have material composites, including the above materials, to achieve various desired characteristics such as strength, rigidity, elasticity, compliance, biomechanical performance, durability and radiolucency or imaging preference. The components of system 30, individually or collectively, may also be fabricated from a heterogeneous material such as a combination of two or more of the above-described materials. The components of system 30 may be monolithically formed, integrally connected or include fastening elements and/or instruments, as described herein.

System 30 is employed, for example, with an open, mini-open or minimally invasive surgical technique to move or apply pressure to a bone fragment, fracture or surface, such as, in treating distal radius fractures. System 30 includes an inflatable bone tamp, such as, for example, an inflatable member 40 extending along a longitudinal axis A between a first end 42 and a second end 44. An inner surface 46 of member 40 defines a passageway 48 extending through end 42 and a chamber 50 in end 44. Passageway 48 extends parallel to axis A and has a cylindrical cross sectional configuration and a uniform diameter along the length of passageway 48. It is envisioned that passageway 48 may be disposed in orientations relative to axis A, such as, for example, transverse, perpendicular and/or other angular orientations such as acute, obtuse, co-axial and/or may be offset or staggered. It is further envisioned that all or only a portion of passageway 48 may be variously configured and dimensioned, such as, for example, planar, concave, convex, hemispherical, polygonal, irregular, uniform, non-uniform, staggered, tapered, consistent or variable, depending on the requirements of a particular application.

Passageway 48 is in communication with chamber 50 such that a material, such as, for example, saline, a contrast solution or compressed air may be inserted through passageway 48 and into chamber 50 to move chamber 50 from a first unexpanded orientation in which chamber 50 has a first diameter to an second expanded orientation in which chamber 50 has a second diameter that is greater than the first diameter.

It is envisioned that chamber 50 can define a single or multi-layered balloon where each balloon layer has the same diameter and/or wall thickness, is comprised of the same material or materials having substantially identical mechanical properties, and has the same degree of molecular orientation in the body portion of the balloon. It will be apparent that in some situations it will be desirable to have some balloon layers having different thicknesses, materials, and/or degree of molecular orientations upon deflation, while at the same time having equivalent size, mechanical properties, and/or orientation upon inflation or expansion. For other applications, it will be apparent that one can vary size, material, and/or orientation to at least some degree, depending upon the requirements of a particular application.

It is contemplated that chamber 50 may be defined by an impenetrable structural layer having low friction surfaces so as to facilitate deployment of member 40 through a surgical instrument, such as, for example, a working cannula and prevent rupture of chamber 50 as it is inflated or expanded in situ. Further variations are contemplated involving different combinations of lubricating layers and structural layers. In some embodiments, structural layers of chamber 50 can contain polyamides, polyesters, polyethylenes, polyurethanes, their co-polymers and combinations thereof.

It is envisioned that chamber 50 can be adapted to withstand the particular stresses, pressures, and deformities to which they might be placed under when inflated or expanded within a surgical site, such as, for example, a bone void in one or more vertebrae. For example, because a top (outer) layer of chamber 50 may be exposed to sharp objects (such as calcified plaque, bone, bone spurs, or other natural protrusions within a patient's body), the top layer could be made from a more compliant material that is scratch and puncture resistant, than the layer or layers below the top layer (inner layer(s)). That is, the top or outer layer is made from a more compliant material that is scratch and puncture resistant and the inner layers of the multi-layer balloon, which are generally not exposed to sharp objects, made from a less compliant material with higher burst strength. It is contemplated that further variations are possible, depending on which stresses, pressures, and deformities the layers must withstand in a particular medical application.

End 44 includes a circular opening 54 that is in communication with chamber 50. Opening 54 extends parallel to axis A. It is contemplated that opening 54 may be disposed at alternate orientations, relative to axis A, such as, for example, transverse, perpendicular and/or other angular orientations such as acute or obtuse, co-axial and/or may be offset or staggered. It is further envisioned that all or only a portion of opening 54 may have alternate cross section configurations, such as, for example, oval, oblong, triangular, square, polygonal, irregular, uniform, non-uniform, offset, staggered, and/or tapered.

In one embodiment, chamber 50 has a substantially rectangular configuration when chamber 50 is in the second orientation. In one embodiment, chamber 50 has a bulbous configuration when chamber 50 is in the second orientation. It is envisioned that all or only a portion of chamber 50 may be variously configured and dimensioned, such as, for example, oval, oblong, triangular, square, polygonal, planar, concave, convex, hemispherical, polygonal, irregular, uniform, non-uniform, staggered, tapered, consistent or variable when chamber 50 is in the second orientation, depending on the requirements of a particular application.

In one embodiment, chamber 50 has an asymmetrical cross sectional configuration when chamber 50 is in the second orientation. That is, a first side of chamber 50 has a diameter that is different from a diameter of an opposite second side of chamber 50. In one embodiment, chamber 50 is formed to have an asymmetrical configuration by providing tubing with a uniform cross-section, such as, for example, a circular cross-section, and molding the tubing with an asymmetric mold. In one embodiment, chamber 50 is formed to have an asymmetrical configuration by extruding tubing having an asymmetric cross-section. In one embodiment, chamber 50 is formed to have an asymmetrical configuration by providing tubing with non-uniform material properties that may be molded within an asymmetric mold, such as, for example, providing tubing having a uniform or asymmetric cross-section, with one side of the tubing being softer than an opposite side of the tubing.

In one embodiment, chamber 50 has a triangular configuration when chamber 50 is in the second orientation. In one embodiment, chamber 50 is formed to have a triangular configuration by providing tubing with a uniform cross-section, such as, for example, a circular cross-section, and molding the tubing with a triangular mold. In one embodiment, chamber 50 is formed to have a triangular configuration by extruding tubing having a triangular cross-section. In one embodiment, chamber 50 is formed to have a triangular configuration by providing tubing with non-uniform material properties that may be molded within an asymmetric mold, such as, for example, providing tubing having a uniform or triangular cross-section, with at least one side of the tubing being softer than at least one opposite side of the tubing.

In one embodiment, chamber 50 includes a first lobe that is spaced apart from a second lobe by a cylindrical section when chamber 50 is in the second orientation. The first and second lobes each have a first diameter when the member 40 is in the first orientation and a second diameter when member 40 is in the second orientation. The cylindrical section has a third diameter when member 40 is in the first orientation and the second orientation. In one embodiment, the third diameter is equal to the first diameter. In one embodiment, the third diameter is less than first diameter. In one embodiment, the third diameter is greater than the first diameter. In one embodiment, the first lobe is inflatable independent of the second lobe and vice versa. This configuration allows one of the first lobe and the second lobe to have the second diameter when member 40 is in the second orientation and the other of first and second lobes to have the first diameter when member 40 is in the second orientation. In one embodiment, a multiple lumen catheter is used such that each of the first and second lobes has access to its own lumen such that each of the first and second lobes can be selectively inflated by delivering fluid through a respective lumen.

An inner member 56 is disposed in passageway 48 and chamber 50 such that member 56 extends through opening 54. Member 56 includes an inner surface 58 defining a second passageway 60. Passageway 60 extends parallel to axis A, has a cylindrical cross sectional configuration and a uniform diameter along the length of passageway 60. It is envisioned that passageway 60 may be disposed in orientations relative to axis A, such as, for example, transverse, perpendicular and/or other angular orientations such as acute, obtuse, co-axial and/or may be offset or staggered. It is further envisioned that all or only a portion of passageway 60 may be variously configured and dimensioned, such as, for example, planar, concave, convex, hemispherical, polygonal, irregular, uniform, non-uniform, staggered, tapered, consistent or variable, depending on the requirements of a particular application.

Member 56 includes a first end 62 and a second end 64 including a circular opening 66 that is in communication with passageway 60. Opening 66 extends parallel to axis A. As shown in FIG. 1, for example, end 64 extends through opening 54. It is contemplated that opening 66 may be disposed at alternate orientations, relative to axis A, such as, for example, transverse, perpendicular and/or other angular orientations such as acute or obtuse, co-axial and/or may be offset or staggered. It is further envisioned that all or only a portion of opening 66 may have alternate cross section configurations, such as, for example, oval, oblong, triangular, square, polygonal, irregular, uniform, non-uniform, offset, staggered, and/or tapered.

In some embodiments, end 44 of member 40 is tethered to the outer surface of member 56 by a method of bonding or attachment, such as, for example, adhesive bonding, thermal bonding, laser bonding or RF bonding. In some embodiments, member 56 and member 40 are integrally formed.

A guide member 70, such as a guide wire or stylet extends between a first end 72 and a second end 74. Member 70 is disposed in passageway 60 such that end 74 extends through opening 66. End 74 is configured to penetrate tissue to fix system 30 relative to the anatomy of a patient, such as, for example, a bone in order to treat a bone disorder, such as, for example, a fracture. In some embodiments, member 70 is a metal wire. It is envisioned that member 70 may also comprise a molded plastic, a stainless steel material or Nitinol. In some embodiments, end 74 includes a trocar tip, a diamond tip, a threaded tip, or another pointed tip to facilitate insertion of end 74 into tissue, such as, for example, bone.

Figure 2:
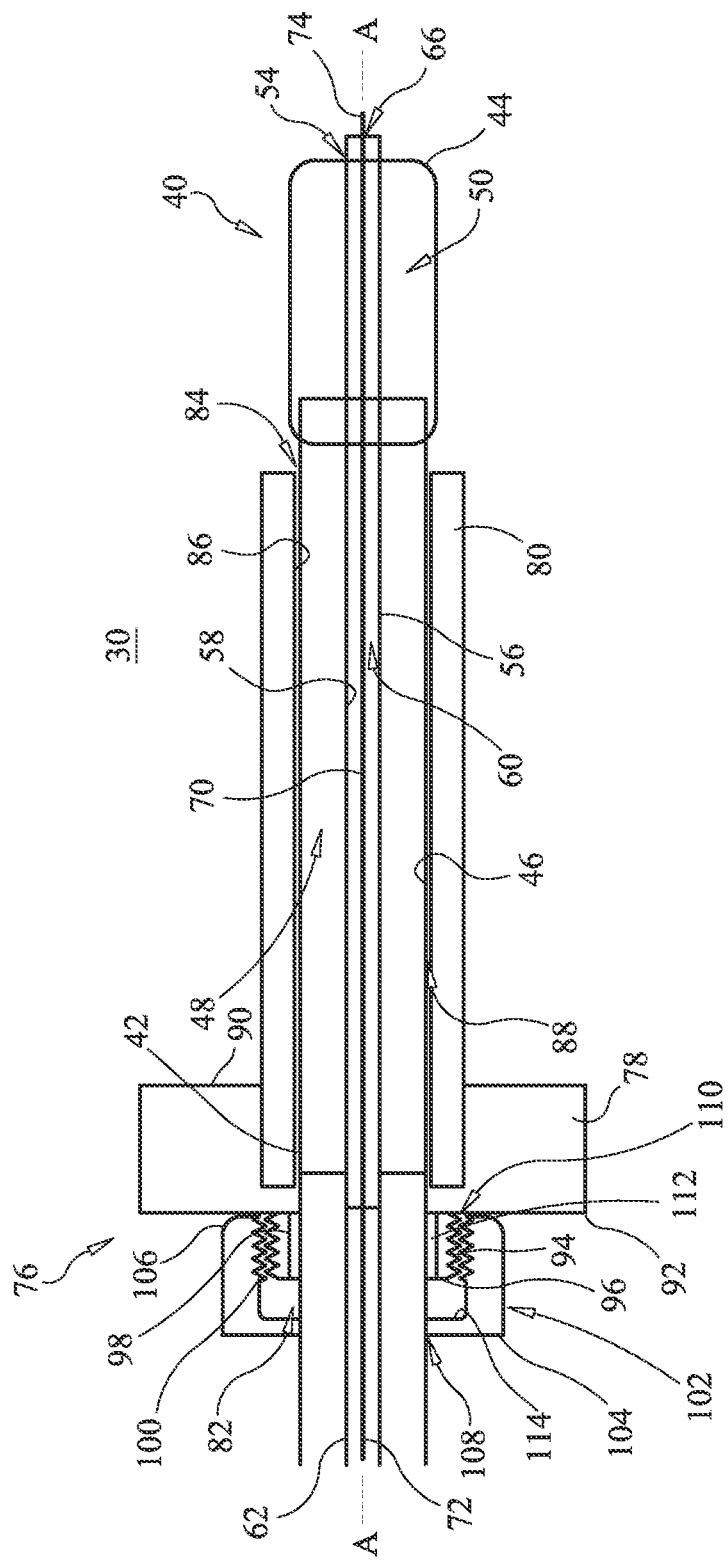
FIG. 2 is a side, cross sectional view of one embodiment of a surgical system in accordance with the principles of the present disclosure.
Figure 4:
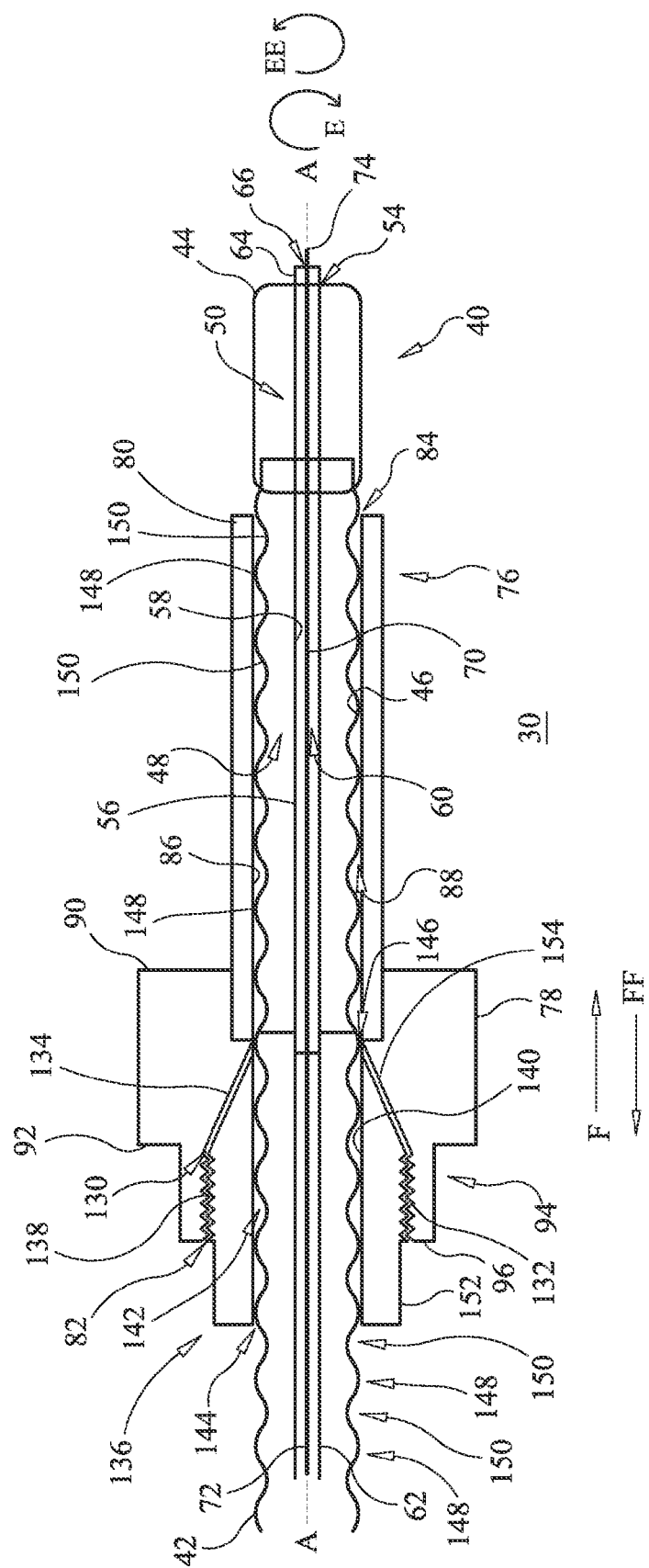
FIG. 4 is a side, cross sectional view of one embodiment of a surgical system in accordance with the principles of the present disclosure.

In some embodiments, as shown in FIGS. 1, 2 and 4, system 30 includes a cannula 76 extending along axis A between a first end, such as, for example, a handle 78 and an opposite second end 80. Cannula 76 includes a circular first opening 82 extending through handle 78 and a circular second opening 84 extending through end 80. Cannula 76 further includes an inner surface 86 defining a passageway 88 extending between handle 78 and end 80 such that passageway 88 is in communication with openings 82, 84. Passageway 88 extends parallel to axis A and has a cylindrical cross sectional configuration with a uniform diameter throughout the length of passageway 88. It is envisioned that all or only a portion of opening 82, opening 84 and/or passageway 88 may have alternate cross section configurations, such as, for example, oval, oblong, triangular, square, polygonal, irregular, uniform, non-uniform, offset, staggered, undulating, arcuate, variable and/or tapered. It is further envisioned that passageway 88 may be disposed at alternate orientations relative to longitudinal axis A, such as, for example, transverse and/or other angular orientations such as acute or obtuse and/or may be offset or staggered and/or may be disposed at alternative angular orientations relative to axis A, depending on the requirements of a particular application.

Handle 78 includes a planar first surface 90 extending transverse to axis A and an opposite planar second surface 92 extending transverse to axis A. Handle 78 further includes a projection 94 extending parallel to axis A from surface 92. Projection 94 includes a planar end face 96 extending perpendicular to axis A. It is envisioned that surface 90 and/or surface 92 may be variously configured and dimensioned, such as, for example, planar, concave, convex, polygonal, irregular, uniform, non-uniform, staggered, tapered, consistent or variable, depending on the requirements of a particular application. In one embodiment the handle is ergonomically shaped. It is further envisioned that surface 90, surface 92, projection 94 and/or end face 96 may be disposed at alternate orientations relative to longitudinal axis A, such as, for example, transverse and/or other angular orientations such as acute or obtuse and/or may be offset or staggered and/or may be disposed at alternative angular orientations relative to axis A, depending on the requirements of a particular application.

In some embodiments, as shown in FIGS. 1 and 2, projection 94 includes a threaded outer surface 98 configured to engage a threaded inner surface 100 of a nut, such as, for example, cap 102. Cap 102 extends between a first end 104 and a second end 106. End 104 includes a first circular opening 108 and end 106 includes a second circular opening 110. Openings 108, 110 extend parallel to axis A and are in communication with surface 100. Member 40 extends through openings 108, 110 such that opening 108 forms a friction fit with an outer surface of member 40 to fix member 40 relative to cap 102. In one embodiment, the threaded portion of the cannula handle incorporates a collet such that when the nut is tightened on the cannula handle, the collet deforms and captures the IBT.

In some embodiments, opening 108 includes a deformable material 112, such as, for example, silicone disposed therein to enhance engagement between cannula 76 and member 40. In some embodiments, material 112 has a tubular configuration such that material 112 can be disposed between the inner surface of projection 94 and the outer surface of member 40, as shown in FIG. 2. It is contemplated that material 112 may be molded into handle 78 or may be a separate piece that interfaces with handle 78. It is envisioned that all or only a portion of material 112 may have alternate cross section configurations, such as, for example, oval, oblong, triangular, square, polygonal, irregular, uniform, non-uniform, offset, staggered, and/or tapered, depending upon the requirements of a particular application.

Engagement of surface 98 with surface 100 and engagement of the outer surface of member 40 with opening 108 allows member 40 to be movable between a first orientation and a second orientation. When member 40 is in the first orientation, surface 100 is spaced apart from surface 98 and member 40 is spaced apart from opening 108 such that member 40 is movable within passageway 88 in the direction shown by arrow C or the direction shown by arrow CC. When member 40 is in the second orientation, surface 100 engages surface 98 and member 40 is disposed within opening 108 such that member 40 is fixed within passageway 88. Member 40 moves between the first orientation and the second orientation by rotating cap 102 about projection 94 in the direction shown by arrow B or the direction shown by arrow BB such that cap 102 translates in the direction shown by arrow C relative to cannula 76. Member 40 moves between the second orientation and the first orientation by rotating cap 102 about projection 94 in the direction shown by arrow B or the direction shown by arrow BB such that cap 102 translates in the direction shown by arrow CC relative to cannula.

Cap 102 includes an unthreaded inner surface defining a planar wall 114 extending transverse to axis A. In some embodiments, face 96 engages wall 114 when surface 98 is fully engaged with surface 100 such that cap 102 is fixed relative to handle 78. It is envisioned that all or only a portion of wall 114 may be variously configured and dimensioned, such as, for example, planar, concave, convex, polygonal, irregular, uniform, non-uniform, staggered, tapered, consistent or variable, depending on the requirements of a particular application. It is further envisioned that wall 114 may be disposed at alternate orientations relative to longitudinal axis A, such as, for example, transverse, perpendicular and/or other angular orientations such as acute or obtuse and/or may be offset or staggered and/or may be disposed at alternative angular orientations relative to axis A, depending on the requirements of a particular application.

In assembly, operation and use, system 30 is employed with a surgical procedure, such as, for a correction or treatment of bone fractures. It is contemplated that one or all of the components of system 30 can be delivered or implanted as a pre-assembled device or can be assembled in situ. System 30 may be completely or partially revised, removed or replaced. For example, system 30 can be employed with a surgical correction treatment of an applicable condition or injury of an affected portion of a patient, such as, for example, a fracture in an arm of a human patient, such as, for example, a Colles' fracture. It is envisioned that system 30 may also be used to treat other affected portions of the patient, such as, for example, a calcaneus bone, bones of the feet or hands, bones of the spine, bones of the arms and legs, etc.

In use, to treat a fracture, a medical practitioner obtains access to a surgical site including the fractured bone in any appropriate manner, such as through incision and retraction of tissues. In one embodiment, a drill is employed to remove bone tissue to provide access to a repair site. It is envisioned that system 30 can be used in any existing surgical method or technique including open surgery, mini-open surgery, minimally invasive surgery and percutaneous surgical implantation, whereby the fractured or injured bone is accessed through a mini-incision or sleeve that provides a protected passageway to the area. Once access to the surgical site is obtained, the particular surgical procedure can be performed for treating the injury or disorder. The configuration and dimension of system 30 is determined according to the configuration, dimension and location of a selected section of the bone fracture and the requirements of a particular application.

An incision is made in the body of a patient and a cutting instrument (not shown) creates a surgical pathway for use of the components of system 30 in the surgical procedure. This may include the use of a cannula or other device. A preparation instrument (not shown) can be employed to prepare tissue surfaces, as well as for aspiration and irrigation of a surgical region according to the requirements of a particular surgical application.

Member 70 may be delivered to a surgical site, such as, for example, a bone disorder, such as, for example a fracture by inserting end 74 into the surgical pathway and translating member 70 until end 74 is disposed in tissue, such as, for example, bone to fix member 70 relative to the bone. Members 40, 56 and cannula 76 are then delivered to the surgical site by positioning member 70 within passageway 60 and translating members 40, 56 and cannula 76 along member 70 until chamber 50 is positioned adjacent the surgical site.

Cap 102 is then positioned relative to projection 94 such that surface 98 is aligned with surface 100. Cap 102 is then rotated about projection 94 in the direction shown by arrow B or the direction shown by arrow BB such that surface 98 engages surface 100 such that cap 102 translates relative to projection 94 in the direction shown by arrow C. Cap 102 is rotated about projection 94 in the direction shown by arrow B or the direction shown by arrow BB until wall 114 engages face 96 and the outer surface of member 40 forms a friction fit with opening 108 such that member 40 is fixed in passageway 70. That is, member 40 is prevented from translating along member 70.

A material, such as, for example, saline, a contrast solution or compressed air may be inserted through passageway 48 and into chamber 50 to move chamber 50 from an unexpanded orientation to an expanded orientation such that chamber 50 creates a void in the bone. After the void is formed in the bone, members 40, 56 and cannula 76 may be removed from the patient and a second cannula inserted into the patient over member 70 such that a distal end of the second cannula is positioned in or adjacent to the void. In the alternative the working cannula can be left in its position and only the IBT is removed doing away with the need for a second cannula. The working cannula can then be used to place the void delivery tool into position to deliver BVF material. Bone filler material is then delivered through the second cannula to deliver bone filler material into the void so as to at least partially fill the void and realign fragments of the fracture and/or elevate collapsed bone to its proper height. It is envisioned that the bone filler material may include autograft, allograft, demineralized bone matrix, mineral composites, blocks, granules and pellets and bone cement, such as, for example, polymethylmethacrylate (PMMA)-based material (Kyphon HV-R, ActivOs, ActivOs 10, Xpede), calcium phosphate (Skaffold, Norian, Hydroset, KyphOs FS) and calcium sulfate (OsteoSet), as well as other injectables.

Figure 3:
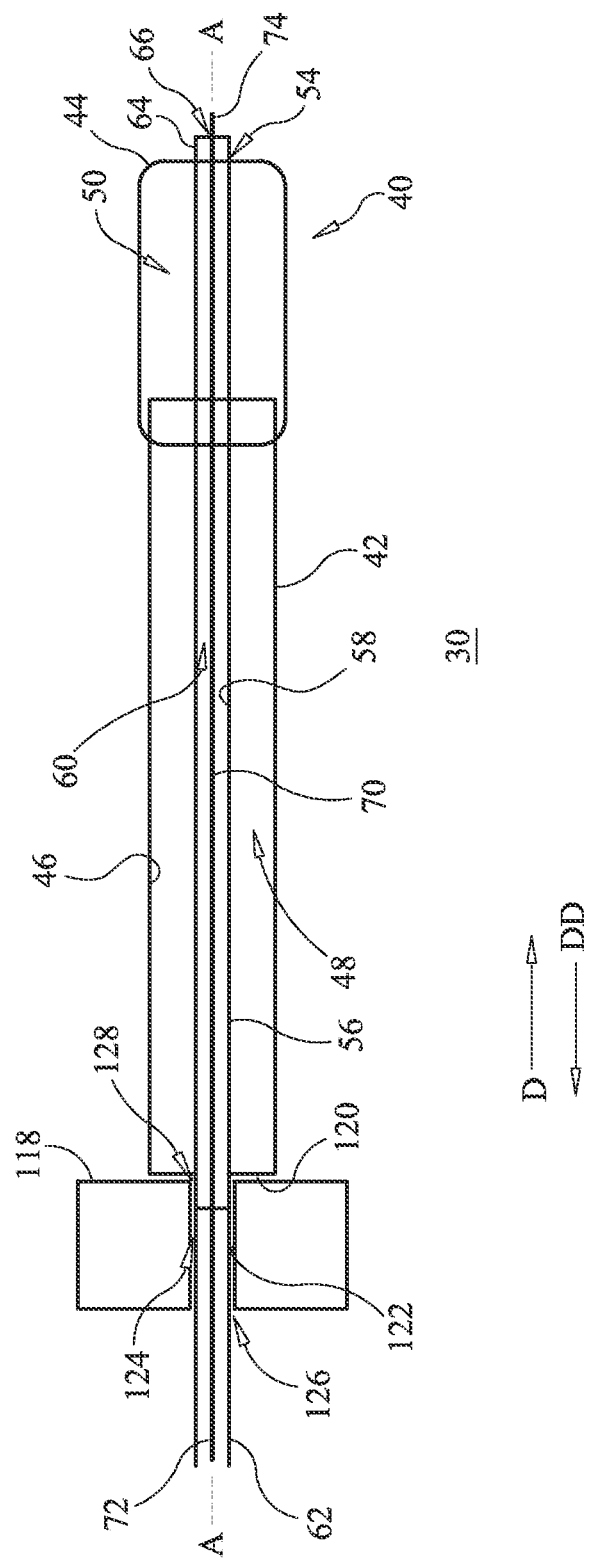
FIG. 3 is a side, cross sectional view of one embodiment of a surgical system in accordance with the principles of the present disclosure.

In one embodiment, shown in FIG. 3, system 30 includes a stopper 116 having a planar distal end surface 118 extending perpendicular to axis A configured to engage a planar proximal end surface 120 of member 40 extending perpendicular to axis A to prevent member 40 from moving proximally relative to member 70. It is envisioned that all or only a portion of surface 118 and/or surface 120 may be variously configured and dimensioned, such as, for example, planar, concave, polygonal, irregular, uniform, non-uniform, staggered, tapered, consistent or variable, depending on the requirements of a particular application. It is further envisioned that all or only a portion of surface 118 and/or surface 120 may be disposed at alternate orientations, relative to axis A, such as, for example, transverse, perpendicular and/or other angular orientations such as acute or obtuse, co-axial and/or may be offset or staggered. It is contemplated that all or only a portion of surface 118 and/or surface 120 may have alternate surface configurations to enhance fixation with surface 118 and/or surface 120 such as, for example, rough, arcuate, undulating, mesh, porous, semi-porous, dimpled and/or textured according to the requirements of a particular application.

Stopper 116 includes an inner surface 122 defining a passageway 124 having member 56 disposed therein. A first end of stopper 116 includes a first opening 126 and a second end of the stopper includes a second opening 128. Openings 126, 128 are in communication with passageway 124. Member 70 extends through openings 126, 128 such that an outer surface of member 70 engages surface 122. In one embodiment, member 40 and stopper 116 are separate components. In one embodiment, member 40 and stopper 116 are integrally formed to prevent member 40 from moving proximally and/or distally relative to member 56.

In use, member 70 may be delivered to a surgical site, such as, for example, a bone disorder, such as, for example a fracture by inserting end 74 into the surgical pathway and translating member 70 until end 74 is disposed in tissue, such as, for example, bone to fix member 70 relative to the bone. Members 40, 56 are then delivered to the surgical site by positioning member 70 within passageway 60 and translating members 40, 56 along member 70 until chamber 50 is positioned adjacent the surgical site. In some embodiments, members 40, 56 are inserted using a cannula, such as, for example, cannula 76 described above.

Stopper 116 is then positioned over member 70 such that member 56 extends through passageway 124. Stopper 116 is then translated relative to member 40 in the direction shown by arrow D until surface 118 engages surface 120 such that member 56 and/or member 40 is prevented from translating along member 70 in the direction shown by arrow DD.

A material, such as, for example, saline, a contrast solution or compressed air may be inserted through passageway 48 and into chamber 50 to move chamber 50 from an unexpanded orientation to an expanded orientation such that chamber 50 creates a void in the bone. After the void is formed in the bone, members 40, 56 may be removed from the patient and a second cannula inserted into the patient over member 70 such that a distal end of the second cannula is positioned in or adjacent the void. In the alternative the working cannula can be left in its position and only the IBT is removed doing away with the need for a second cannula. The working cannula can then be used to place the void delivery tool into position to deliver BVF material. Bone filler material is then delivered through the second cannula to deliver bone filler material into the void so as to at least partially fill the void and realign fragments of the fracture and/or elevate collapsed bone to its proper height. It is envisioned that the bone filler material may include autograft, allograft, demineralized bone matrix, mineral composites, blocks, granules and pellets and bone cement, such as, for example, polymethylmethacrylate (PMMA)-based material (Kyphon HV-R, ActivOs, ActivOs 10, Xpede), calcium phosphate (Skaffold, Norian, Hydroset, KyphOs FS) and calcium sulfate (OsteoSet), as well as other injectables.

In one embodiment, shown in FIG. 4, an inner surface of handle 78 defines a passageway 130 having a threaded first portion 132 extending parallel to axis A and an unthreaded second portion 134 extending at an acute angle relative to axis A. It is envisioned that portion 132 and/or portion 134 may be disposed at alternate orientations relative to axis A, such as, for example, transverse, perpendicular and/or other angular orientations such as acute or obtuse and/or may be offset or staggered and/or may be disposed at alternative angular orientations relative to axis A, depending on the requirements of a particular application.

An anchor member 136 is disposed in passageway 130. Member 136 includes a threaded outer surface 138 configured to engage portion 132 to fix member 136 relative to handle 78. Member 136 includes an inner surface 140 defining a passageway 142 having the member 40 disposed therein. Member 136 includes a first opening 144 extending through a first end of member 136 and a second opening 146 extending through a second end of member 136. Opening 146 has a first diameter that is less than a second diameter of opening 144. Openings 144, 146 are in communication with passageway 142.

The outer surface of member 40 includes a series of convexly curved first portions 148 having a third diameter between opposite portion 148 connected to one another by a series of concavely curved second portions 150 having a fourth diameter between opposite portions 150 such that member 40 has a beaded or undulating configuration. The third diameter (of portions 148) is greater than the first diameter (of opening 146) and the fourth diameter (of portions 150) is less than the first diameter (of opening 146).

Member 136 includes at least one slot (not shown) extending parallel to axis A through inner and outer surfaces of member 136 adjacent opening 146. It is envisioned that member 136 may include on or a plurality of slots. The slots allow member 136 to move from a first orientation in which opening 146 has a first width and a second orientation in which opening 146 has a second width that is greater than the first width. Portions 148 are permitted to move through opening 146 when member 136 is in the first orientation, but are prevented from moving through opening 146 when member 136 is in the second orientation. Force must therefore be applied to move portions 148 through opening 146. That is, a force greater than a force exerted by inflation of member 40 is required to move member 136 from the first orientation to the second orientation. It is envisioned that all or only a portion of portion 148 and/or portion 150 may be variously configured and dimensioned, such as, for example, planar, concave, convex, polygonal, irregular, uniform, non-uniform, staggered, tapered, consistent or variable, depending on the requirements of a particular application.

The outer surface of member 136 includes a first section 152 extending parallel to axis A and a second section 154 extending at an acute angle relative to axis A. Section 152 includes surface 138. Section 152 engages portion 132 and section 154 engages portion 134. It is envisioned that section 152 and/or section 154 may be disposed at alternate orientations relative to axis A, such as, for example, transverse, perpendicular and/or other angular orientations such as acute or obtuse and/or may be offset or staggered and/or may be disposed at alternative angular orientations relative to axis A, depending on the requirements of a particular application.

In use, member 70 may be delivered to a surgical site, such as, for example, a bone disorder, such as, for example a fracture by inserting end 74 into the surgical pathway and translating member 70 until end 74 is disposed in tissue, such as, for example, bone to fix member 70 relative to the bone. Members 40, 56 and cannula 76 are then delivered to the surgical site by positioning member 70 within passageway 60 and translating members 40, 56 and cannula 76 along member 70 until chamber 50 is positioned adjacent the surgical site.

Member 136 is then positioned relative to projection 94 such that surface 138 is aligned with portion 132. Member 136 is then rotated relative to projection 94 in the direction shown by arrow E or the direction shown by arrow EE such that surface 138 engages portion 132 such that member 136 translates relative to projection 94 in the direction shown by arrow F. Member 136 keeps member 40 in place until member 136 is loosened. When member 136 is loosened, member 40 may be translated through passageway 88 in the direction shown by arrow F or the direction shown by arrow FF. After member 40 is positioned relative to member 56, member 70, cannula 76 and/or member 136, the force may be discontinued such that member 136 moves from the first orientation to the second orientation and member 40 is fixed relative to member 56, member 70, cannula 76 and/or member 136.

A material, such as, for example, saline, a contrast solution or compressed air may be inserted through passageway 48 and into chamber 50 to move chamber 50 from an unexpanded orientation to an expanded orientation such that chamber 50 creates a void in the bone. After the void is formed in the bone, members 40, 56 and cannula 76 may be removed from the patient and a second cannula inserted into the patient over member 70 such that a distal end of the second cannula is positioned in or adjacent the void. In the alternative the working cannula (cannula 76) can be left in its position and the IBT (member 40) is removed doing away with the need for a second cannula. The working cannula can then be used to place the void delivery tool into position to deliver BVF material. Bone filler material is then delivered through the second cannula to deliver bone filler material into the void so as to at least partially fill the void and realign fragments of the fracture and/or elevate collapsed bone to its proper height. It is envisioned that the bone filler material may include autograft, allograft, demineralized bone matrix, mineral composites, blocks, granules and pellets and bone cement, such as, for example, polymethylmethacrylate (PMMA)-based material (Kyphon HV-R, ActivOs, ActivOs 10, Xpede), calcium phosphate (Skaffold, Norian, Hydroset, KyphOs FS) and calcium sulfate (OsteoSet), as well as other injectables.

In one embodiment, system 30 includes an agent, which may be disposed, packed or layered within, on or about the components and/or surfaces of the components of system 30. It is envisioned that the agent may include bone growth promoting material, such as, for example, bone graft to enhance fixation of the fixation elements with the bone in need of repair. It is further contemplated that the agent may include therapeutic polynucleotides or polypeptides. It is further contemplated that the agent may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. The components of system 30 can be made of radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto. For example, all or a portion of member 40, including chamber 50 can be modified or extended to accommodate particular formulations of balloon construction materials or fabrication techniques. Different balloon materials and surface coatings, or outer layers of different materials or surface coatings may also be applied to member 40 and/or chamber 50 to facilitate a smaller balloon profile, biocompatibility, lubrication as well as other properties. The embodiments above can also be modified so that some features of one embodiment are used with the features of another embodiment. One skilled in the art may find variations of these preferred embodiments, which, nevertheless, fall within the spirit of the present invention, whose scope is defined by the claims set forth below.

What is claimed is:

1. A device for performing a surgical procedure on a patient, the device defining a longitudinal axis, the device comprising:
   an inflatable member extending along the longitudinal axis, the inflatable member being inflatable between a first substantially uninflated position and a second substantially inflated position, and including a proximal end having a first opening, a distal end having a second opening, the first opening defining an entrance to an inner surface of the inflatable member, the inner surface defining a first passageway extending from the proximal end to the distal end, the second opening defining an exit from the inflatable member, and a chamber, the chamber defining a multi-layered balloon, each layer having one of substantially a same diameter and substantially a same wall thickness;
   an inner member extending along the longitudinal axis, the inner member being disposed in the first passageway and extending through the first and second openings, the inner member including an inner surface defining a second passageway, a proximal end of the inner member including a third opening, and a distal end of the inner member including a fourth opening, the fourth opening of the inner member passing through the second opening of the inflatable member, the third and fourth openings of the inner member being in communication with the second passageway, the distal end of the inflatable member being bonded to an outer surface of the inner member;
   a guide member disposed in the second passageway and extending through at least the third and fourth openings of the inner member;
   an outer member extending along the longitudinal axis substantially surrounding the inner member, the outer member comprising a proximal end having a projection including a threaded outer surface, and an inner surface defining a third passageway, the third passageway being configured to house the inflatable member therein, when the inflatable member is in the first substantially uninflated position; and
   a cap including a threaded inner surface engaging the threaded outer surface of the projection;
   wherein at least the inflatable member is movable along the longitudinal axis between the first substantially uninflated position within at least the third passageway, and the second substantially inflated position exterior to the third passageway.

2. A device as recited in claim 1, wherein the cap includes a first opening in a proximal end of the cap and a second opening in a distal end of the cap, the inflatable member extending through the first and second openings of the cap such that an outer surface of the inflatable member forms a friction fit with the second opening of the cap, thereby fixing the cap relative to the inflatable member.

3. A device as recited in claim 2, wherein:
   the outer member moves between a first orientation and a second orientation by rotating the cap about the projection in a first direction; and
   the outer member moves between the second orientation and the first orientation by rotating the cap about the projection in a second direction that is opposite the first direction.

4. A device as recited in claim 1, wherein the inflatable member, in the first substantially uninflated position has a first diameter and the inflatable member in the second substantially inflated position has a second diameter, the second diameter being greater than the first diameter.

5. A device as recited in claim 4, wherein the second diameter is greater than a maximum diameter of the third passageway.

6. A device as recited in claim 1, wherein the proximal end of the outer member comprises a handle having a first surface extending substantially transverse to the longitudinal axis and an opposite second surface extending substantially transverse to the longitudinal axis, the projection extending substantially parallel to the longitudinal axis from the second surface.

7. A device as recited in claim 1, wherein:
the projection includes an end face extending substantially transverse to the longitudinal axis;
the threaded inner surface extends substantially parallel to the longitudinal axis;
the cap includes an unthreaded inner surface defining a wall extending substantially transverse to the longitudinal axis; and
the end face engages the wall when the threaded inner surface is substantially fully engaged with the threaded outer surface.

8. A device as recited in claim 1, wherein at least a portion of the third passageway includes a deformable material comprising silicone disposed between the third passageway and an outer surface of the inflatable member.

9. A device as recited in claim 8, wherein the deformable material is disposed in the projection.

10. A device as recited in claim 1, wherein the inflatable member has a plurality of selected cross-sectional configurations, each selected cross-sectional configuration of the plurality of selected cross-sectional configurations having a dimension and a configuration substantially matching a dimension and a configuration of at least one bone defect in the patient.

11. A device for performing a surgical procedure on a patient, the device defining a longitudinal axis, the device comprising:
an inflatable member extending along the longitudinal axis, the inflatable member being inflatable between a first substantially uninflated position and a second substantially inflated position, and including a proximal end having a first opening, a distal end having a second opening, the first opening defining an entrance to an inner surface of the inflatable member, the inner surface defining a first passageway extending from the proximal end to the distal end, the second opening defining an exit from the inflatable member, and a chamber, the chamber defining a multi-layered balloon, each layer having one of substantially a same diameter and substantially a same wall thickness;
an inner member extending along the longitudinal axis, the inner member being disposed in the first passageway and extending through the opening, the inner member including an inner surface defining a second passageway, a distal end of the inner member having at least a third opening, the at least the third opening being in communication with the second passageway, the distal end of the inflatable member being bonded to an outer surface of the inner member;
an outer member extending along the longitudinal axis substantially surrounding the inner member, the outer member comprising a proximal end, and an inner surface defining a third passageway, the third passageway being configured to house the inflatable member therein, when the inflatable member is in the first substantially uninflated position;
a guide member disposed in the second passageway and extending through the at least the third opening of the inner member; and
a stopper that engages the inflatable member to prevent the inflatable member from moving proximally relative to the guide member;
wherein at least the inflatable member is movable along the longitudinal axis between the first substantially uninflated position within at least the third passageway, and the second substantially inflated position exterior to the third passageway.

12. A device as recited in claim 11, wherein a distal end surface of the stopper engages a proximal end surface of the inflatable member.

13. A device as recited in claim 11, wherein:
an inner surface of the stopper defines a passageway having the inner member disposed therein;
a proximal end of the stopper includes a fourth opening and a distal end of the stopper includes a fifth opening;
the fourth and fifth openings of the stopper being in communication with a fourth passageway defined by the stopper; and
the inner member extends through the fourth and fifth openings of the stopper.

14. A device as recited in claim 11, wherein the inflatable member and the stopper are configured to prevent the inflatable member from moving distally relative to the inner member.

15. A device for performing a surgical procedure on a patient, the device defining a longitudinal axis, the device comprising:
an inflatable member extending along the longitudinal axis between a proximal end having a first opening and a distal end having a second opening, the first end defining an entrance to an inner surface of the inflatable member, the inner surface defining a first passageway extending from the proximal end to the distal end, the second opening defining an exit from the inflatable member, and a chamber;
an inner member extending along the longitudinal axis, the inner member being disposed in the first passageway and extending through the first and second openings, the inner member including an inner surface defining a second passageway, a proximal end of the inner member including a third opening, and a distal end of the inner member having a fourth opening, the fourth opening of the inner member passing through the second opening of the inflatable member, the third and fourth openings of the inner member being in communication with the second passageway, the distal end of the inflatable member being bonded to an outer surface of the inner member;
a guide member disposed in the second passageway and extending through at least the third and openings of the inner member;
an outer member extending along the longitudinal axis substantially surrounding the inner member, the outer member comprising a proximal end having an inner surface, the inner surface defining a third passageway extending through the proximal end of the outer member, the proximal end of the outer member including a projection, the projection having a threaded first portion and an unthreaded second portion, a distal end of the outer member including an inner surface defining a fourth passageway, the fourth passageway being in communication with the third passageway, the inflatable member extending through the fourth passageway; and an anchor member disposed in the third passageway including a threaded outer surface engaging the threaded first portion, the anchor member including an inner surface defining a fifth passageway having the inflatable member disposed therein;

wherein at least the inflatable member is movable along the longitudinal axis between the first substantially uninflated position within at least the third passageway, and the second substantially inflated position exterior of the third passageway.

16. A device as recited in claim 15, wherein:
the anchor member includes a fifth opening extending through a proximal end of the anchor member and a sixth opening extending through a distal end of the anchor member, the fifth and sixth openings of the anchor member being in communication with the third and fourth passageways; and
the fifth opening of the anchor member has a diameter that is less than a maximum diameter of the proximal end of the inflatable member.

17. A device as recited in claim 15, wherein:
the anchor member includes a fifth opening extending through a proximal end of the anchor member and a sixth opening extending through a distal end of the anchor member, the fifth and sixth openings of the anchor member being in communication with the third and fourth passageways;
the fifth opening of the anchor member is circular and has a first diameter; and
an outer surface of the inflatable member includes a series of first portions having a second diameter connected to one another by a series of second portions having a third diameter, the second diameter being greater than the first diameter and the third diameter being less than the first diameter.

18. A device as recited in claim 17, wherein:
the first portion extends substantially parallel to the longitudinal axis; and
the second portion extends at a substantially acute angle relative to the longitudinal axis.

19. A device as recited in claim 18, wherein:
the anchor member further includes a first section extending substantially parallel to the longitudinal axis and a second section extending at a substantially acute angle relative to the longitudinal axis, the first section including a threaded outer surface;
the first section is disposed in the first portion; and
the second section is disposed in the second portion.

20. A device as recited in claim 15, wherein the inflatable member, in the first substantially uninflated position has a first diameter and the inflatable member, in the second substantially inflated position has a second diameter, the second diameter being greater than the first diameter.

21. A device as recited in claim 10, wherein the inflatable member having the selected cross-sectional configuration, in the substantially inflated position, has a volume, the volume being one of equal to and greater than a volume of the bone defect in the patient.

* * * * *

UNITED STATES PATENT AND TRADEMARK OFFICE
CERTIFICATE OF CORRECTION

| | | |
|---|---|---|
| PATENT NO. | : 9,204,915 B2 | Page 1 of 1 |
| APPLICATION NO. | : 13/830537 | |
| DATED | : December 8, 2015 | |
| INVENTOR(S) | : Arthur et al. | |

It is certified that error appears in the above-identified patent and that said Letters Patent is hereby corrected as shown below:

On the title page item (74), under "Attorney, Agent, or Firm", in Column 2, Line 1, delete "Sorell Lenna & Schmidt" and insert -- Sorell, Lenna & Schmidt, --, therefor.

In the specification,

In Column 6, Line 46, delete "polyaetide," and insert -- polyketide, --, therefor.

In Column 6, Line 47, delete "polycaroplaetohe" and insert -- polycaprolactone --, therefor.

In Column 12, Lines 8-9, delete "passageway 70." and insert -- passageway 60. --, therefor.

Signed and Sealed this
Twenty-first Day of June, 2016

Michelle K. Lee
*Director of the United States Patent and Trademark Office*